United States Patent
Kobayashi (10) Patent No.: US 9,979,911 B2
(45) Date of Patent: May 22, 2018

(54) IMAGE PROCESSING APPARATUS, RADIATION IMAGING APPARATUS, IMAGE PROCESSING METHOD, AND STORAGE MEDIUM FOR DARK CORRECTION

(71) Applicant: CANON KABUSHIKI KAISHA, Tokyo (JP)

(72) Inventor: Tsuyoshi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 35 days.

(21) Appl. No.: 15/172,638

(22) Filed: Jun. 3, 2016

(65) Prior Publication Data

US 2016/0366353 A1     Dec. 15, 2016

(30) Foreign Application Priority Data

Jun. 12, 2015   (JP) .................. 2015-119711

(51) Int. Cl.
| | |
|---|---|
| *H04N 9/64* | (2006.01) |
| *H04N 5/361* | (2011.01) |
| *H04N 5/378* | (2011.01) |
| *A61B 6/00* | (2006.01) |

(52) U.S. Cl.
CPC ........... *H04N 5/361* (2013.01); *A61B 6/5205* (2013.01); *A61B 6/5258* (2013.01); *H04N 5/378* (2013.01); *A61B 6/487* (2013.01)

(58) Field of Classification Search
CPC .............................. H04N 5/361; A61B 6/5258
See application file for complete search history.

(56) References Cited

U.S. PATENT DOCUMENTS

| | | | | |
|---|---|---|---|---|
| 8,639,010 B2* | 1/2014 | Adachi | ................. | A61B 6/585 128/922 |
| 2003/0210344 A1* | 11/2003 | Bloom | ................. | H04N 5/361 348/362 |
| 2016/0366352 A1 | 12/2016 | Kobayashi | | |

FOREIGN PATENT DOCUMENTS

JP     2010-012082 A     1/2010

* cited by examiner

*Primary Examiner* — Gary C Vieaux
(74) *Attorney, Agent, or Firm* — Carter, DeLuca, Farrell & Schmidt, LLP (57) ABSTRACT

An image processing apparatus includes: a dark correction unit configured to obtain a dark corrected image by removing a dark image obtained in a state without radiation irradiation from an object image obtained by radiation irradiation; an addition value obtaining unit configured to analyze pixel values included in a plurality of dark corrected images and, based on an analysis result of the pixel values including a negative pixel value, obtain an addition value used to correct the negative pixel value; and an adding unit configured to add the addition value to the pixel values of the dark corrected image.

22 Claims, 6 Drawing Sheets

IMAGE PROCESSING APPARATUS, RADIATION IMAGING APPARATUS, IMAGE PROCESSING METHOD, AND STORAGE MEDIUM FOR DARK CORRECTION

BACKGROUND OF THE INVENTION

Field of the Invention

The present invention relates to an image processing apparatus, a radiation imaging apparatus, an image processing method, and a storage medium.

Description of the Related Art

In recent years, a radiation imaging apparatus that two-dimensionally arranges image sensors (detection elements) made of amorphous silicon or single-crystal silicon and captures a radiation image has been put into practical use. In such a radiation imaging apparatus, as processing for reducing the influence of fixed pattern noise caused by the dark current and the like of the image sensors, dark correction processing of subtracting a dark image obtained in a state without radiation irradiation from an object image is performed.

The fixed pattern noise output is known to vary in accordance with an increase/decrease in the dark current caused by a variation in the operation temperature. For this reason, if the fixed pattern noise varies during the time from dark image capturing to object image capturing, uncorrected fixed pattern noise may remain in the object signal and lead to a loss of the contrast of the object signal, or the object signal may be lost by overcorrection.

For example, in a case in which fixed pattern noise decreases, and overcorrection occurs, a pixel having a negative pixel value smaller than 0 is generated in an image after dark correction. When performing logarithmic conversion in image processing after dark correction, an irreversible information loss may occur in object information upon replacing a region including a negative pixel value with positive values. To prevent an information loss in correction, Japanese Patent Laid-Open No. 2010-12082 proposes a technique of shifting entire image data to the positive side in a case in which the minimum pixel value is negative so that the minimum pixel value changes to 0.

However, in the arrangement for performing analysis on an image basis, as in Japanese Patent Laid-Open No. 2010-12082, even if the same object is captured, the shift amount (correction amount) varies in each image due to the influence of random noise and the like in the apparatus. In a case in which the same object is continuously captured as in fluoroscopy, if the shift amount (correction amount) varies in each frame, and the tone of an output image varies like a flicker, it may exert an effect on image processing after dark correction, resulting in degradation in image quality.

The present invention has been made in consideration of the above-described problem, and provides an image processing technique capable of reducing a variation in the correction amount between in each image and suppressing degradation in quality of an output image while preventing a loss of image information.

SUMMARY OF THE INVENTION

According to one aspect of the present invention, there is provided an image processing apparatus comprising: a dark correction unit configured to obtain a dark corrected image by removing a dark image obtained in a state without radiation irradiation from an object image obtained by radiation irradiation; an addition value obtaining unit configured to analyze pixel values included in a plurality of dark corrected images and, based on an analysis result of the pixel values including a negative pixel value, obtain an addition value used to correct the negative pixel value; and an adding unit configured to add the addition value to the pixel values of the dark corrected image.

According to another aspect of the present invention, there is provided an image processing apparatus comprising: a dark correction unit configured to obtain a dark corrected image by removing a dark image obtained in a state without radiation irradiation from an object image obtained by radiation irradiation; an evaluation value obtaining unit configured to analyze pixel values included in the dark corrected image and obtain an analysis result of the pixel values including a negative pixel value as an evaluation value; a statistic information obtaining unit configured to obtain statistic information based on a plurality of evaluation values obtained along with an elapse of time; an addition value obtaining unit configured to obtain an addition value used to correct the negative pixel value based on a variation in the evaluation values with respect to the statistic information; and an adding unit configured to add the addition value to the pixel values of the dark corrected image.

According to still another aspect of the present invention, there is provided an image processing method comprising: obtaining a dark corrected image by removing a dark image obtained in a state without radiation irradiation from an object image obtained by radiation irradiation; analyzing pixel values included in a plurality of dark corrected images and, based on an analysis result of the pixel values including a negative pixel value, obtaining an addition value used to correct the negative pixel value; and adding the addition value to the pixel values of the dark corrected image.

According to yet another aspect of the present invention, there is provided an image processing method comprising: obtaining a dark corrected image by removing a dark image obtained in a state without radiation irradiation from an object image obtained by radiation irradiation; analyzing pixel values included in the dark corrected image and obtaining an analysis result of the pixel values including a negative pixel value as an evaluation value; obtaining statistic information based on a plurality of evaluation values obtained along with an elapse of time; obtaining an addition value used to correct the negative pixel value based on a variation in the evaluation values with respect to the statistic information; and adding the addition value to the pixel values of the dark corrected image.

According to the present invention, it is possible to provide an image processing technique capable of reducing a variation in the correction amount in each image and suppressing degradation in quality of an output image while preventing a loss of image information.

Further features of the present invention will become apparent from the following description of exemplary embodiments (with reference to the attached drawings).

DESCRIPTION OF THE EMBODIMENTS

Preferred embodiments of the present invention will now be described in detail with reference to the accompanying drawings. Note that the constituent elements described in the embodiments are merely examples. The technical scope of the present invention is determined by the scope of claims and is not limited by the following individual embodiments.

First Embodiment

Figure 1:
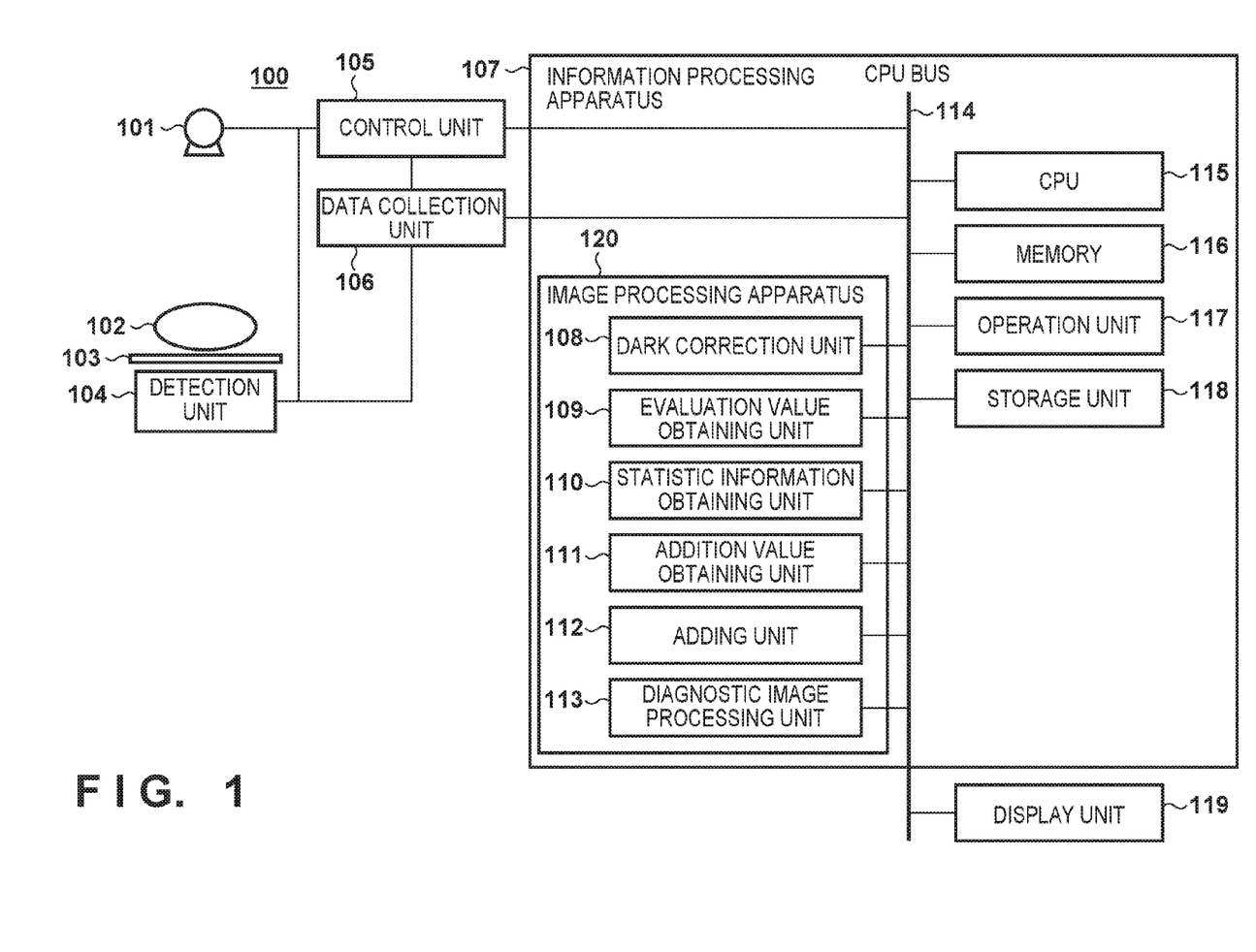
FIG. 1 is a block diagram showing the basic arrangement of an image processing apparatus.

The arrangement of an image processing apparatus according to the first embodiment will be described with reference to FIG. 1. FIG. 1 is a block diagram showing the basic arrangement of an image processing apparatus 120 according to this embodiment. The arrangement of a radiation imaging apparatus 100 including the image processing apparatus 120 is shown as an example. The arrangement shown in FIG. 1 will also be referred to as a radiation imaging system. In this embodiment, radiation includes not only X-rays but also α-rays, β-rays, γ-rays, and the like that are beams generated by particles (including photons) emitted by radioactive decay, and additionally, beams having equivalent energy or more, for example, particle rays and cosmic rays.

The radiation imaging apparatus 100 includes a radiation generator 101 that generates radiation, a placement unit 103 (bed) used to place an object 102, and a detection unit 104 that detects radiation. The detection unit 104 outputs image data corresponding to radiation that has passed through the object 102. The detection unit 104 includes an image sensor in which, for example, solid-state image sensors made of amorphous silicon or single-crystal silicon are two-dimensionally arranged. The detection unit 104 converts the detected radiation into digital data, and outputs it as image data.

The radiation imaging apparatus 100 also includes a control unit 105, a data collection unit 106 that collects various kinds of data, an information processing apparatus 107 that performs image processing or control of the entire device in accordance with a user instruction, and a display unit 119 that displays an image output from the information processing apparatus 107. The information processing apparatus 107 includes the image processing apparatus 120 that processes image data detected by the detection unit.

The control unit 105 (control apparatus) can control the radiation generator 101, the detection unit 104, and the data collection unit 106 (data collection apparatus). The control unit 105 (control apparatus) controls the timing of radiation generation of the radiation generator 101 and the imaging conditions of the radiation generator 101. Under the control of the control unit 105, the detection unit 104 performs radiation detection processing in synchronism with the timing of radiation irradiation of the radiation generator 101, converts detected radiation into digital data, and outputs it as image data.

Under the control of the control unit 105, the data collection unit 106 collects various kinds of digital data from the detection unit 104, and transmits the collected data to the image processing apparatus 120 in the information processing apparatus 107. The data collection unit 106 can thin image data pixels in accordance with a predetermined transmission rate and transmit the thinned image data to the image processing apparatus 120. For example, the transmission rate can be decided based on the ratio of all pixel data of the detection unit 104 and pixel data necessary for display of the display unit 119.

The information processing apparatus 107 includes a CPU 115 that controls each constituent element, a memory 116 that temporarily stores various kinds of data, an operation unit 117, a storage unit 118 that stores various kinds of image data, and the image processing apparatus 120. The constituent elements of the information processing apparatus 107 are electrically connected via a CPU bus 114 and can mutually transmit/receive data.

The memory 116 stores various kinds of data and programs necessary for processing of the CPU 115, and also includes a work memory for the operation of the CPU 115. The CPU 115 controls the operations of the information processing apparatus 107, the image processing apparatus 120, and the radiation imaging apparatus 100, and the like using the memory 116 in accordance with a user instruction input to the operation unit 117.

When the operation unit 117 receives a user instruction, an object is irradiated with radiation, and image obtaining is performed under the general control of the CPU 115. The radiation generator 101 irradiates the object 102 with radiation under predetermined imaging conditions, and the radiation that has passed through the object 102 is detected by the detection unit 104. The control unit 105 controls the imaging conditions such as a voltage, a current, and an irradiation time for the radiation generator 101. The radiation generator 101 generates radiation under predetermined imaging conditions. The information of the radiation detected by the detection unit 104 is converted into digital data and collected by the data collection unit 106 (data collection apparatus) as image data.

The image data collected by the data collection unit 106 and transmitted is input to the image processing apparatus 120 via the CPU bus 114 in the information processing apparatus 107. When the image data transmitted from the data collection unit 106 is input to the image processing apparatus 120, the components of the image processing apparatus 120 perform image processing, and the image that has undergone the image processing is output.

The image processing apparatus 120 includes a dark correction unit 108, an evaluation value obtaining unit 109, a statistic information obtaining unit 110, an addition value obtaining unit 111, an adding unit 112, and a diagnostic image processing unit 113. Note that in this embodiment, the image processing apparatus 120 is mounted on the information processing apparatus 107. However, the embodiment is not limited to this arrangement. For example, the image processing apparatus 120 may be independent of the information processing apparatus 107, or the apparatus that performs dark correction may include a dedicated CPU and memory. Alternatively, the arrangement of the image processing apparatus 120 may be provided in the data collection unit 106 or the control unit 105, and image processing may be executed in the data collection unit 106 or the control unit 105.

Figure 2:
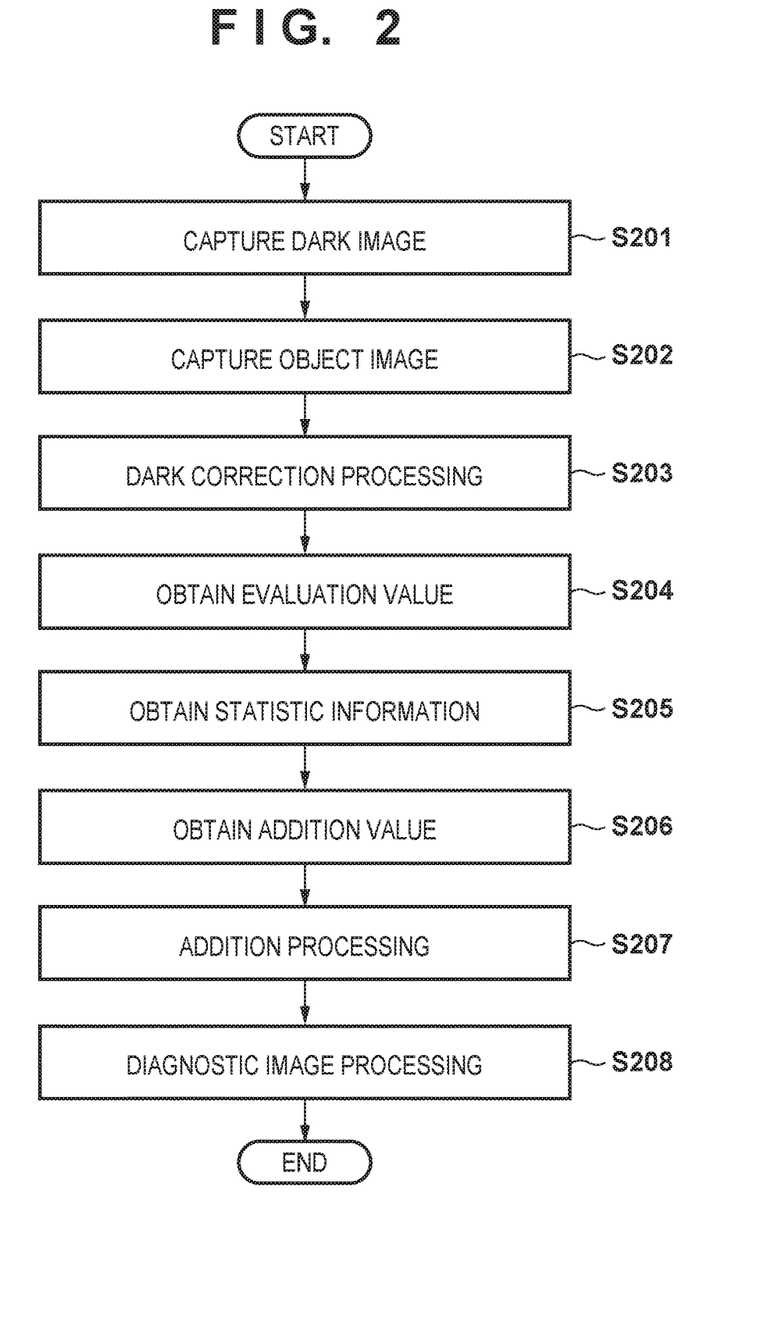
FIG. 2 is a flowchart for explaining the procedure of processing performed by the image processing apparatus.

The operation of the radiation imaging apparatus 100 and the operation of the image processing apparatus 120 included in the radiation imaging apparatus 100 will be described next with reference to FIGS. 2 to 5. FIG. 2 is a flowchart for explaining the procedure of processing performed by the image processing apparatus 120.

In step S201, the radiation imaging apparatus 100 captures a dark image in a state without radiation irradiation under the control of the control unit 105. The detection unit 104 performs a charge accumulation operation in a state without radiation irradiation (non-exposure state), and outputs an image based on the accumulated charges as a dark image. The dark image is an image including fixed pattern noise (the fixed output component of the detection unit) caused by the dark current and the like of the solid-state image sensors. The data collection unit 106 collects the dark image including the fixed pattern noise. The data collection unit 106 transmits the collected dark image to the information processing apparatus 107. The dark image transmitted by the data collection unit 106 is transferred to the storage unit 118 via the CPU bus 114 and saved.

Note that to reduce the influence of noise included in the dark image, the detection unit 104 of the radiation imaging apparatus 100 can capture a plurality of dark images (first dark images), and the dark correction unit 108 of the image processing apparatus 120 can average the characteristics of the plurality of captured dark images and use the result for dark correction.

The amount of fixed pattern noise (the fixed output component of the detection unit) is known to vary depending on the accumulation time at the time of imaging. For this reason, a case in which the object image capturing time (charge accumulation time) is not constant because of the difference in the operation mode or frame rate at the time of imaging may occur as in a case in which, for example, a moving image capturing is performed. In this case, dark images corresponding to a plurality of different accumulation times may be captured and saved in the storage unit 118 in this step. In this case, the dark correction unit 108 obtains information representing imaging conditions such as an operation mode and a frame rate at the time of imaging from the control unit 105. The dark correction unit 108 can obtain dark images corresponding to the imaging conditions from the storage unit 118 and use them in dark correction processing (step S203).

In step S202, the radiation imaging apparatus 100 irradiates the object with radiation and captures an object image. According to a user instruction received via the operation unit 117, the control unit 105 controls to synchronously perform the radiation irradiation operation of the radiation generator 101 and the accumulation operation of the detection unit 104. The object image captured by the detection unit 104 is collected by the data collection unit 106. The data collection unit 106 transmits the collected object image to the information processing apparatus 107. The transmitted object image data is input to the image processing apparatus 120 via the CPU bus 114 under the control or the CPU 115.

In step S203, the dark correction unit 108 in the image processing apparatus 120 obtains a dark corrected image by removing the dark image obtained in a state without radiation irradiation from the object image obtained by radiation irradiation (dark correction processing). More specifically, the dark correction unit 108 executes dark correction processing in accordance with $$W_i = X_i - D \quad (1)$$

where $X_i$ represents an ith object image obtained after the start of imaging, D represents a dark image, and $W_i$ represents an image (dark corrected image) after dark correction. The dark correction unit 108 subtracts the dark image D from the object image $X_i$, thereby removing the fixed pattern noise (the fixed output component of the detection unit) of a dark current included in the object image $X_i$. Note that each of the dark corrected image $W_i$, the object image $X_i$, and the dark image D represents the linear output of the detection unit 104 (sensor). In addition, the dark corrected image $W_i$ obtained by the difference (subtraction) between the object image $X_i$ and the dark image D sometimes includes a negative value. The storage unit 118 that stores the dark corrected image $W_i$ can store signed information.

Figure 3:
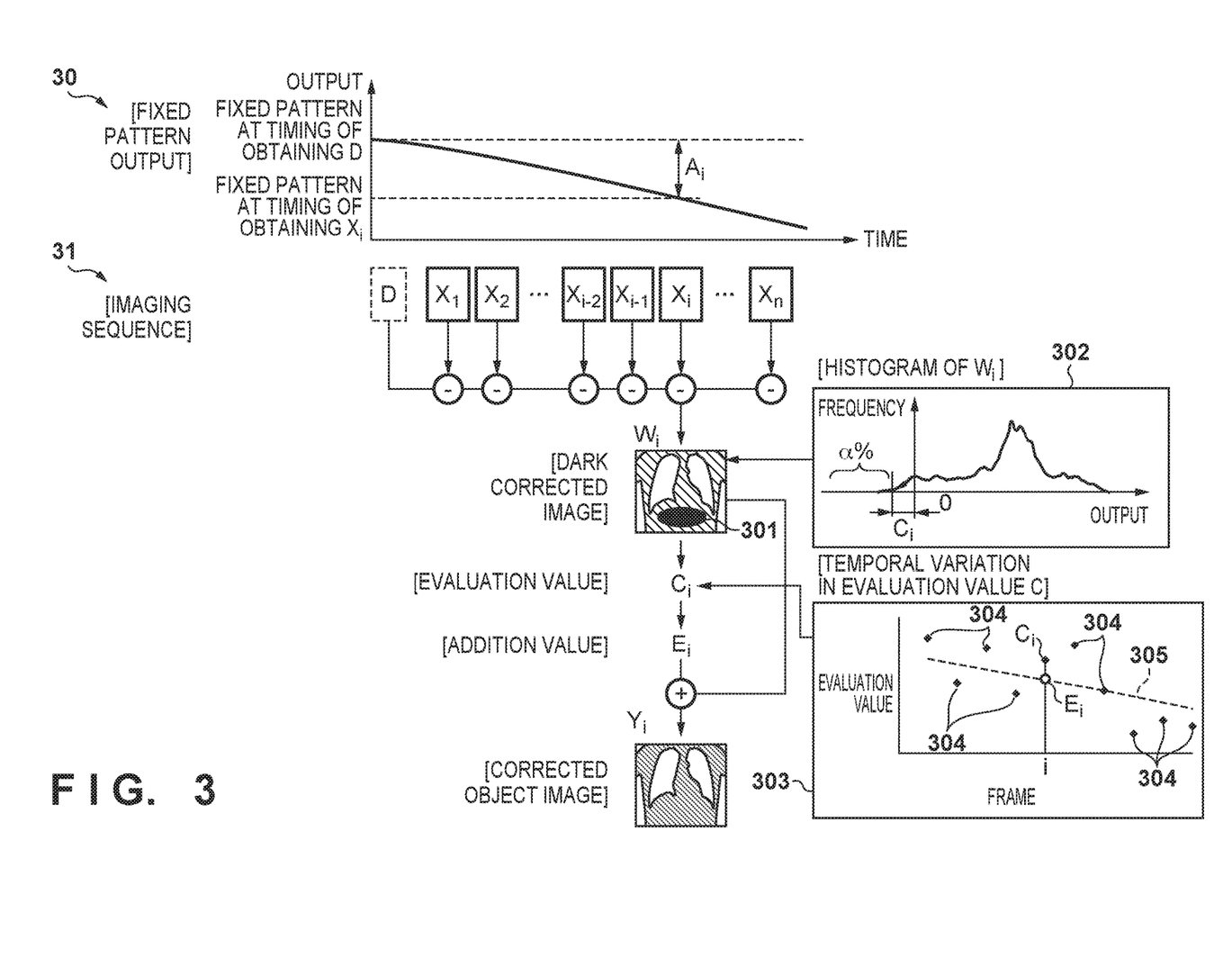
FIG. 3 is a schematic view for explaining the operation of the image processing apparatus.

FIG. 3 is a schematic view for explaining the operation of the image processing apparatus 120. Referring to FIG. 3, reference numeral 30 indicates a variation in fixed pattern noise (the fixed output component of the detection unit) when performing a series of imaging operations. Reference numeral 31 indicates a sequence of imaging of the dark image D and the object image $X_i$.

As indicated by the reference numeral 30 in FIG. 3, consider a case in which using the capturing time of the dark image D as the point of reference, the fixed pattern noise output (the fixed output component of the detection unit) varies and decreases by $A_i$ during the time from capturing of the dark image D to obtaining of the object image $X_i$. The fixed pattern noise output changes along with the elapse of time. Hence, in the dark correction processing of step S203, it is impossible to perform correction in consideration of the fixed pattern noise output that has varied along with the elapse of time from dark image capturing (step S201) to object image capturing (step S202).

For this reason, if a portion where the signal of the object image $X_i$ (the pixel value of a pixel) is smaller than that of the dark image D is generated in a portion of the object image (a region where the signal level is low), a region 301 (FIG. 3) where the pixel value of a pixel is smaller than 0 may be generated as pixel information in the dark corrected image $W_i$ obtained by the difference between the object image $X_i$ and the dark image D. Since it is difficult to directly measure the variation $A_i$ in the fixed pattern noise (the fixed output component of the detection unit) during imaging, processing of estimating the variation $A_i$ in the fixed pattern noise from image information obtained in association with imaging and correcting the variation $A_i$ in the fixed pattern noise is necessary.

In step S204, the evaluation value obtaining unit 109 in the image processing apparatus 120 analyzes pixel values included in the plurality of dark corrected images, and obtains the analysis result of the pixel values including a negative pixel value as an evaluation value. For example, the evaluation value obtaining unit 109 analyzes pixel values included in the dark corrected images, and obtains the analysis result of a predetermined ratio of pixel values including a negative pixel value as an evaluation value. More specifically, for the pixels included in the plurality of dark corrected images $W_i$, the evaluation value obtaining unit 109 analyzes the information of each pixel whose pixel value is smaller than 0. Based on the analysis result, the evaluation value obtaining unit 109 obtains, as an evaluation value $C_i$, an addition value used to correct the pixel value of each pixel whose pixel value is smaller than 0 in the dark corrected image $W_i$. Processing of obtaining the evaluation value $C_i$ (evaluation value obtaining processing) corresponds to the processing of estimating the variation $A_i$ in the fixed pattern noise (the fixed output component of the detection unit) from image information obtained in association with imaging. The procedure of processing performed by the evaluation value obtaining unit 109 will be described below with reference to FIG. 4.

(Processing of Evaluation Value Obtaining Unit 109)

Figure 4:
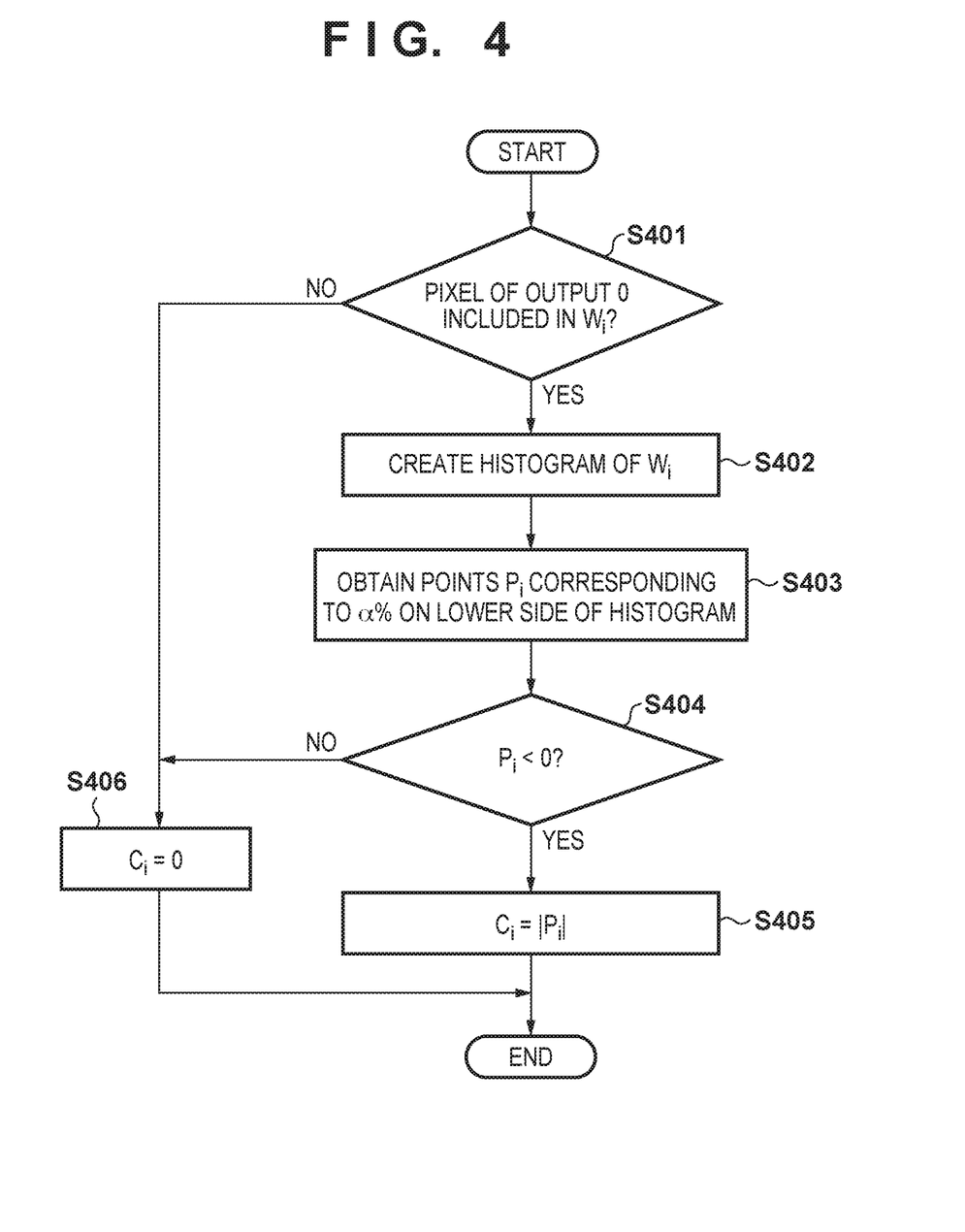
FIG. 4 is a flowchart for explaining the procedure of processing performed by an evaluation value obtaining unit.

In this processing, if a dark corrected image includes a negative pixel value smaller than 0, the evaluation value obtaining unit 109 generates a histogram of pixel values for the dark corrected image, and obtains the pixel values of points corresponding to a predetermined ratio from the lower side of the histogram. The evaluation value obtaining unit 109 then obtains an evaluation value based on a result of determining whether an obtained pixel value is a negative value smaller than 0.

First, in step S401, the evaluation value obtaining unit 109 analyzes whether the dark corrected image $W_i$ includes a pixel whose pixel value is smaller than 0. If the dark corrected image does not include a negative pixel value, the evaluation value obtaining unit 109 obtains an evaluation value set to 0. More specifically, if the dark corrected image $W_i$ does not include a pixel having a pixel value smaller than 0 (NO in step S401), the evaluation value obtaining unit 109 determines that there is no risk to lose pixel information by dark correction processing, and advances the process to step S406. In step S406, the evaluation value obtaining unit 109 sets evaluation value $C_i$=0, and ends the processing.

On the other hand, upon determining in step S401 that the dark corrected image $W_i$ includes a pixel having a pixel value smaller than 0 (YES in step S401), the evaluation value obtaining unit 109 advances the process to step S402.

In step S402, the evaluation value obtaining unit 109 creates a histogram concerning the pixel values of the pixels of the dark corrected image $W_i$. Reference numeral 302 in FIG. 3 indicates a histogram created by the evaluation value obtaining unit 109. Note that the evaluation value obtaining unit 109 can create a histogram after excluding, from all pixels of the detection unit, pixel values in a region where the radiation is blocked. For example, the evaluation value obtaining unit 109 can create a histogram after excluding, by a known technique, a region that is blocked by a collimator or the like and is obviously excluded from the diagnosis target in the image.

In step S403, the evaluation value obtaining unit 109 multiplies the total number of pixels of the detection unit that detects radiation by the predetermined ratio, and specifies the pixel values of points corresponding to the predetermined ratio. That is, the evaluation value obtaining unit 109 obtains values $P_i$ of points corresponding to α % (predetermined ratio) on the lower side of the histogram. $P_i$ is a signed value and is discriminated from the evaluation value $C_i$ that always takes a value of 0 or more as an addition value. Here, α is information representing the ratio of pixels whose pixel values are smaller than 0 after $C_i$ is added to the dark corrected image $W_i$. That is, the information α is information representing a tolerance for a loss in a case in which pixel information is lost by dark correction processing. The information α can arbitrarily be set via the operation unit 117.

Setting α=0 corresponds to setting the minimum value out of the pixel values of the pixels of the dark corrected image $W_i$ to $C_i$. In this case, if a low pixel value is unexpectedly generated due to the influence of random noise of the detection unit or the like, the value $C_i$ may abruptly become high as compared to the pixel values, and overcorrection may be performed.

If an extremely small number of pixels attain pixel values smaller than 0 and lose pixel information in a diagnostic image output from the radiation imaging apparatus, random noise in the detection unit 104 and a change in the value $C_i$ can hardly be discriminated, and the influence on the diagnosability/usefulness of the object image is limited. Hence, a more practical apparatus can be provided by permitting a loss of only a small part of object information and thus reducing the influence of overcorrection.

The evaluation value obtaining unit 109 can set the tolerance (α) for a loss in accordance with the type of an object or the number of pixels or noise characteristic of the detection unit 104. For example, if the detection unit 104 is formed from 3000×3000 pixels, as a permissible range representing the tolerance for a loss, the evaluation value obtaining unit 109 can set α=0.000005 (permitting a loss of information of 45 pixels) to 0.005 (permitting a loss of 450 pixels). The evaluation value obtaining unit 109 can arbitrarily set the permissible range representing the tolerance for a loss by setting the lower and upper limits of the tolerance (α) for a loss.

If an obtained pixel value is smaller than 0 based on the determination result, the evaluation value obtaining unit 109 obtains the absolute value of the pixel value as an evaluation value. More specifically, in step S404, the evaluation value obtaining unit 109 determines, for $P_i$ obtained in step S403, whether $P_i$<0. Upon determining that $P_i$<0 (YES in step S404), the evaluation value obtaining unit 109 advances the process to step S405.

In step S405, the evaluation value obtaining unit 109 sets the absolute value of $P_i$ as the evaluation value $C_i$. That is, the evaluation value obtaining unit 109 sets $C_i$=|$P_i$|, and ends the processing.

On the other hand, if an obtained pixel value is 0 or more based on the determination result, the evaluation value obtaining unit 109 obtains an evaluation value set to 0. More specifically, upon determining in step S404 that $P_i$≥0 (NO in step S404), the evaluation value obtaining unit 109 advances the process to step S406. That is, if $P_i$ is 0 or more ($P_i$≥0), the evaluation value obtaining unit 109 determines that the number of pixels that lose information is equal to or less than the tolerance (falls within the permissible range) even without addition processing of $C_i$. In step S406, the evaluation value obtaining unit 109 sets evaluation value $C_i$=0, and ends the processing.

The evaluation value obtaining unit 109 executes the processes of steps S401 to S406 described above, thereby obtaining the evaluation value $C_i$ from the histogram of the dark corrected image $W_i$, as indicated by the histogram 302 in FIG. 3.

Referring back to FIG. 2, the process of step S205 will be described. In this step, the statistic information obtaining unit 110 obtains statistic information based on a plurality of evaluation values obtained along with the elapse of time. That is, the statistic information obtaining unit 110 executes processing of calculating the statistic of the evaluation values $C_i$ in a plurality of frames. The evaluation values $C_i$ obtained in step S204 are obtained by analyzing the dark corrected image $W_i$. Hence, even in a case in which the same object is captured by fluoroscopy, the evaluation value may vary depending the image due to the influence of noise or the motion of the object under imaging. The variation $A_i$ in the fixed pattern noise (the fixed output component of the detection unit) that should be corrected rarely abruptly varies between neighboring frames. This is because fluoroscopy is often done at a high frame rate of, for example, 15 FPS, but in general, a variation in the temperature or fixed pattern noise output within 1/15 sec is very small. For this reason, if correction is done for an abrupt variation in a pixel value based on an evaluation value C 304 that varies along with the elapse of time, as indicated by a temporal variation 303 of the evaluation values $C_i$ in FIG. 3, the tone of an output image varies like a flicker, the correction amount may vary between frames, and the tone of an output image may vary like a flicker. To obtain an addition value E 305 that hardly varies like a flicker, the statistic information obtaining unit 110 obtains the statistic of the evaluation values $C_i$ that vary along with the elapse of time.

As the statistic information used to measure a time-rate change in the plurality of evaluation values $C_i$, the statistic information obtaining unit 110 can obtain the average value, standard deviation, or the like of the evaluation values $C_i$ in frames of several sec before an evaluation target frame. Note that the average value and the standard deviation as the statistic information are merely examples, and the statistic information obtaining unit 110 can obtain various kinds of statistic information. In addition, the statistic information obtaining unit 110 can set the number of frames to be used to obtain the statistic information in accordance with the size of a storage memory, the frame rate, or the imaging technique.

Figure 5:
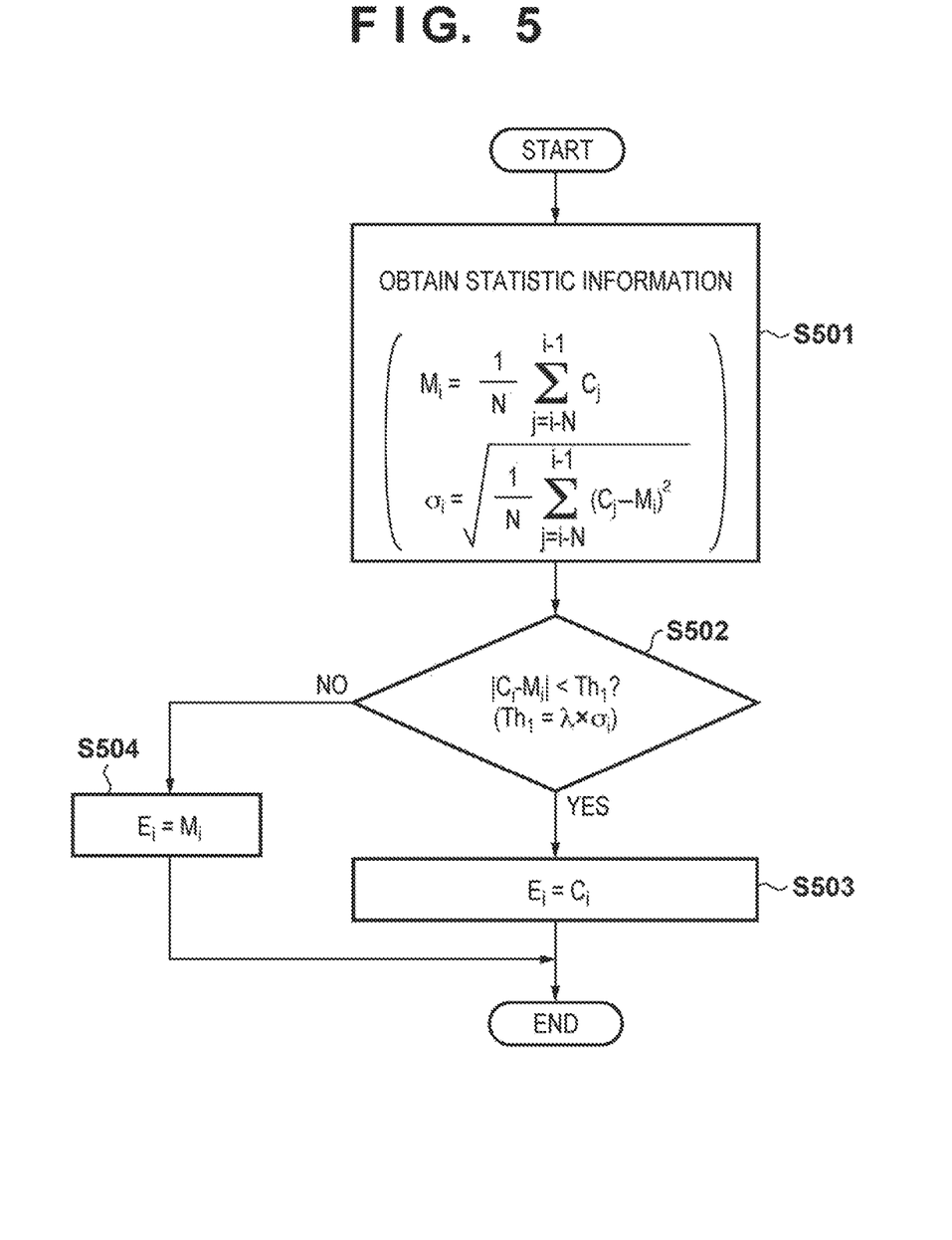
FIG. 5 is a flowchart for explaining the procedure of processing performed by a statistic information obtaining unit and an addition value obtaining unit.

In step S206, the addition value obtaining unit 111 obtains an addition value used to correct a negative pixel value based on the variation in the evaluation values with respect to the statistic information. More specifically, the addition value obtaining unit 111 obtains an addition value $E_i$ used to correct a negative pixel value based on a result of determining whether the variation in the evaluation values $C_i$ with respect to the statistic information obtained by the statistic information obtaining unit 110 exceeds a threshold. FIG. 5 is a flowchart for explaining the procedure of processing of the statistic information obtaining unit 110 and the addition value obtaining unit 111. Processing (addition value obtaining processing) of obtaining an addition value using, as statistic information, the average value and the standard deviation of the evaluation values $C_i$ in frames of several sec before an evaluation target frame will be described here with reference to FIG. 5.

First, the statistic information obtaining unit 110 obtains an average value based on the evaluation values of a plurality of frames captured in the past and a standard deviation based on the evaluation values as statistic information, and obtains a threshold based on the standard deviation. More specifically, in step S501, the statistic information obtaining unit 110 performs calculation to obtain statistic information, and obtains the average value of the evaluation values and a standard deviation based on the evaluation values as statistic information. The statistic information obtaining unit 110 obtains an average value $M_i$ of the evaluation values C of (i−N)th to (i−1)th frames by $$M_i = \frac{1}{N} \sum_{j=i-N}^{i-1} C_j \qquad (2)$$

and obtains a standard deviation $\sigma_i$ based on the evaluation values by $$\sigma_i = \sqrt{\frac{1}{N} \sum_{j=i-N}^{i-1} (C_j - M_i)} \qquad (3)$$

The statistic information obtaining unit 110 can decide the value N in accordance with the size of a storage memory, the frame rate, or the imaging technique. Note that the statistic information obtaining unit 110 can arbitrarily set the value N to, for example, N=10 or more.

Next, the addition value obtaining unit 111 obtains an addition value used to correct a negative pixel value based on a result of determining whether the absolute value of the difference between the average value and the evaluation value of the current frame as the processing target exceeds a threshold. That is, if the variation in the evaluation values with respect to the statistic information does not exceed the threshold based on the determination result of step S502, the addition value obtaining unit 111 obtains, as the addition value, the evaluation value obtained by the evaluation value obtaining unit 109. More specifically, in step S502, the addition value obtaining unit 111 performs threshold processing of the evaluation value $C_i$. The addition value obtaining unit 111 can obtain a threshold $Th_1$ based on the standard deviation $\sigma_i$ by $$Th_1 = \lambda \times \sigma_i \qquad (4)$$

where $\lambda$ is a coefficient that decides the degree of permitting a variation from the average value $M_i$. The addition value obtaining unit 111 can set a value according to the characteristic of the object or tone processing as $\lambda$. Upon determining that the absolute value of the difference between the average value $M_i$ and the evaluation value $C_i$ of the frame is smaller than the threshold $Th_1$ (YES in step S502), the addition value obtaining unit 111 advances the process to step S503.

In step S503, the addition value obtaining unit 111 sets the addition value to the evaluation value. That is, the addition value obtaining unit 111 sets addition value $E_i$=evaluation value $C_i$, and ends the processing.

On the other hand, if the variation in the evaluation values with respect to the statistic information is equal to or large than the threshold based on the determination result of step S502, the addition value obtaining unit 111 obtains, as the addition value, the statistic information obtained by the statistic information obtaining unit 110. More specifically, upon determining that the absolute value of the difference between the average value $M_i$ and the evaluation value $C_i$ of the frame is equal to or larger than the threshold $Th_1$ (NO in step S502), the addition value obtaining unit 111 determines that an impermissible amount of evaluation value variation has occurred, and advances the process to step S504. In step S504, the addition value obtaining unit 111 sets the addition value to the average value. That is, the addition value obtaining unit 111 sets addition value $E_i$=average value $M_i$, and ends the processing.

The statistic information obtaining unit 110 obtains the statistic by the process of step S501 described above. The addition value obtaining unit 111 performs threshold processing in step S502. In addition, the addition value obtaining unit 111 performs the processes to steps S503 and S504, thereby obtaining the addition value $E_i$.

Note that as for the threshold processing of step S502, the threshold $Th_1$ is obtained from the standard deviation $\sigma_i$. However, the embodiment is not limited to this. For example, a threshold that makes a flicker visually unproblematic may be determined in advance as a fixed value in accordance with the characteristic of the detection unit 104, the type of the object, or the imaging method and used. In addition, the addition value obtaining unit 111 may compare not the difference between the average value $M_i$ and the evaluation value $C_i$ of the frame but, for example, the difference between the frame $C_i$ and a frame $C_{i-1}$ before the frame $C_i$ with the threshold $Th_1$.

In the processes of equations (2) and (3), the statistic information obtaining unit 110 obtains the average value $M_i$ and the standard deviation $\sigma_i$ from the evaluation values C of the (i−N)th to (i−1)th frames. However, the processing of this embodiment is not limited to this example. The statistic information obtaining unit 110 may obtain the statistic information using the obtained addition value in place of the evaluation values C. For example, in a case in which the addition value is obtained in step S503 or S504, and after that, the processing shown FIG. 5 is recursively executed for a subsequent frame, in step S501, the statistic information obtaining unit 110 can obtain statistic information based on the addition value E obtained by the previous processing. In this case, the statistic information obtaining unit 110 can obtain the average value $M_i$ and the standard deviation $\sigma_i$ by $$M_i = \frac{1}{N} \sum_{j=i-N}^{i-1} E_j \qquad (5)$$

$$\sigma_i = \sqrt{\frac{1}{N} \sum_{j=i-N}^{i-1} (E_j - M_i)^2} \qquad (6)$$

Referring back to FIG. 2, in step S207, the adding unit 112 adds the addition value to the pixel values of the dark corrected image. That is, the adding unit 112 adds the addition value $E_i$ obtained in step S206 to the pixel values of the dark corrected image $W_i$, and obtains an object image $Y_i$ (corrected object image) in which the pixels having pixel values smaller than 0 are corrected, by $$Y_i = W_i + E_i = X_i - D + E_i \qquad (7)$$

The adding unit 112 outputs the image obtained by correcting the fixed pattern noise (the fixed output component of the detection unit: D) and the variation in the fixed pattern noise in the object image $X_i$ by the addition value $E_i$ as the corrected object image $Y_i$.

In step S208, the corrected object image $Y_i$ is input to the diagnostic image processing unit 113. The diagnostic image processing unit 113 performs preprocessing such as logarithmic conversion processing, gain correction, and defect correction for the corrected object image $Y_i$. After that, the diagnostic image processing unit 113 applies various kinds of enhancement processing and tone conversion processing and then outputs an image (diagnostic image) for diagnosis. Note that the image processes of the diagnostic image processing unit 113 are not limited to the above examples, and another known image processing can be applied to the corrected object image $Y_i$.

According to this embodiment, it is possible to provide an image processing technique capable of reducing a variation in the correction amount in each image and suppressing degradation in quality of an output image while preventing a loss of image information after dark correction.

Second Embodiment

The arrangement of an image processing apparatus according to the second embodiment will be described next. The apparatus according to this embodiment has the same basic arrangement as that in FIG. 1 described in the first embodiment. The processing procedure of the image processing apparatus according to this embodiment is also common to the processing procedure of the image processing apparatus according to the first embodiment in many points. Hence, a detailed description of overlapping arrangements and processes will be omitted, and points of difference from the first embodiment will mainly be described.

In the image processing apparatus according to the second embodiment, processing of an addition value obtaining unit 111 is different from that described in the first embodiment. In this embodiment, pixel values included in a plurality of dark corrected images are analyzed, and the addition value obtaining unit 111 obtains an addition value used to correct a negative pixel value based on the analysis result of pixel values including a negative pixel value. An evaluation value obtaining unit analyzes the pixel values included in the plurality of dark corrected images, and obtains the analysis result of the pixel values including a negative pixel value as an evaluation value. The addition value obtaining unit 111 obtains the addition value used to correct a negative pixel value based on the analysis result (a variation in evaluation values caused by the elapse of time). More specifically, the addition value obtaining unit 111 obtains the addition value used to correct a negative pixel value based on a result of determining whether the variation in the evaluation values caused by the elapse of time exceeds a threshold. Processing of the addition value obtaining unit 111 according to the second embodiment will be described next with reference to FIG. 6.

Figure 6:
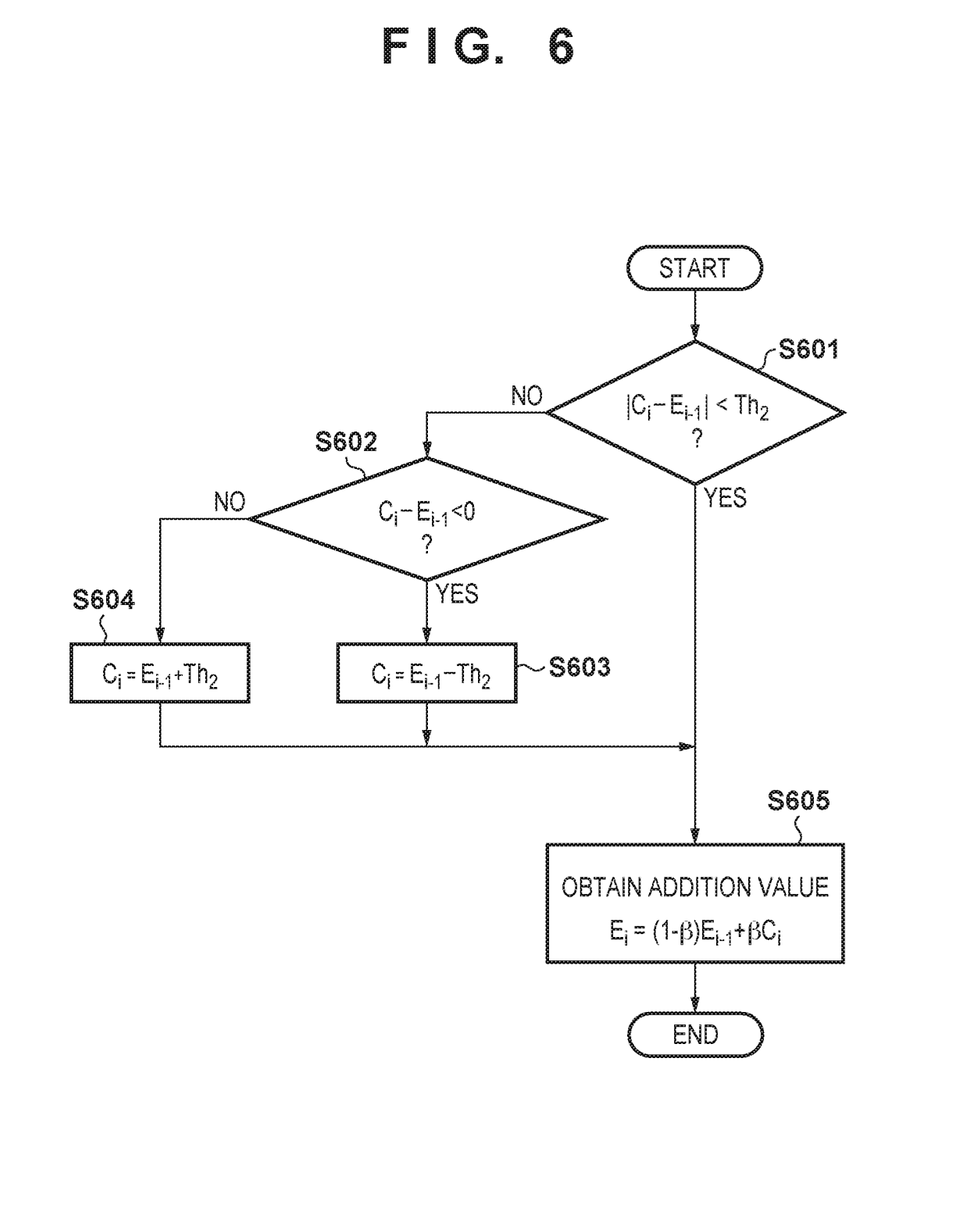
FIG. 6 is a flowchart for explaining the procedure of addition value obtaining processing according to the second embodiment.

FIG. 6 is a flowchart for explaining the procedure of addition value obtaining processing according to the second embodiment. The addition value obtaining unit 111 obtains the difference between the evaluation value of the current frame as the processing target and the addition value of the preceding frame to the current frame, and obtains the addition value of the current frame based on a result of determining whether the absolute value of the difference exceeds a threshold.

More specifically, first in step S601, the addition value obtaining unit 111 performs threshold processing of an evaluation value $C_i$. A threshold $Th_2$ is a coefficient that decides the degree of permitting a variation in the evaluation value $C_i$. The addition value obtaining unit 111 can set a value based on the characteristic of the object or tone processing as the threshold $Th_2$. In this embodiment, the addition value obtaining unit 111 can obtain an addition value $E_i$ by $$\begin{cases} E_1 = C_1 & (i = 1) \\ E_i = (1 - \beta)E_{i-1} + \beta C_i & (i = 2, 3, \ldots) \end{cases} \qquad (8)$$

where $\beta$ is a predetermined weight coefficient.

The addition value obtaining unit 111 can obtain the addition value $E_i$ by applying a recursive filter to an addition value $E_{i-1}$ of the ith preceding frame. This value corresponds to a value obtained by removing a variation in values (noise) from an evaluation value C and temporally smoothing the result. The addition value obtaining unit 111 sets the initial value of an addition value $E_1$ as $C_1$, and recursively executes processing for each frame.

If the absolute value of the difference between the evaluation value $C_i$ of the frame as the processing target and the addition value $E_{i-1}$ of the preceding frame is equal to or larger than the threshold $Th_2$ in step S601 (NO in step S601), the addition value obtaining unit 111 determines that the evaluation value $C_i$ is an unexpected value, and advances the process to step S602.

If the absolute value of the difference between the evaluation value of the current frame and the addition value of the preceding frame to the current frame is equal to or larger than the threshold, and the difference between the evaluation value of the current frame and the addition value of the preceding frame is a negative value smaller than 0, the addition value obtaining unit 111 corrects the evaluation value of the current frame based on a value obtained by subtracting the threshold from the addition value of the preceding frame. That is, if the difference between $C_i$ and $E_{i-1}$ is negative in step S602 (if the difference is smaller than 0: YES in step S602), the addition value obtaining unit 111 advances the process to step S603. In step S603, the addition value obtaining unit 111 sets the evaluation value to $C_i=E_{i-1}-Th_2$, and advances the process to step S605.

On the other hand, if the absolute value of the difference between the evaluation value of the current frame and the addition value of the preceding frame to the current frame is equal to or larger than the threshold, and the difference between the evaluation value of the current frame and the addition value of the preceding frame is 0 or more, the addition value obtaining unit 111 corrects the evaluation value of the current frame based on a value obtained by adding the threshold to the addition value of the preceding frame.

That is, upon determining in step S602 that the difference between $C_i$ and $E_{i-1}$ is 0 or more (NO in step S602), the addition value obtaining unit 111 advances the process to step S604. In step S604, the addition value obtaining unit 111 sets the evaluation value to $C_i=E_{i-1}+Th_2$, and advances the process to step S605.

Upon determining in step S601 that the absolute value of the difference between the evaluation value $C_i$ of the frame as the processing target and the addition value $E_{i-1}$ of the preceding frame is smaller than the threshold $Th_2$ (YES in step S601), the addition value obtaining unit 111 advances the process to step S605 without correcting the evaluation value $C_i$.

In step S605, the addition value obtaining unit 111 executes addition value obtaining processing in accordance with equations (8). If the absolute value of the difference between the evaluation value of the current frame and the addition value of the preceding frame to the current frame does not exceed the threshold (YES in step S601), the addition value obtaining unit 111 obtains the addition value of the current frame based on the addition value of the preceding frame and the evaluation value of the current frame.

On the other hand, if the absolute value of the difference between the evaluation value of the current frame and the addition value of the preceding frame to the current frame is equal to or larger than the threshold (NO in step S601), the addition value obtaining unit 111 obtains the addition value of the current frame based on the addition value of the preceding frame and the corrected evaluation value. In this case, if the evaluation value $C_i$ has been corrected in step S603 or S604, the addition value obtaining unit 111 obtains an addition value E using the corrected evaluation value $C_i$.

According to this embodiment, it is possible to improve the processing speed or reduce the memory capacity to be used by reducing the operation load to obtain the evaluation value or statistic information, in addition to the effects of the first embodiment.

The embodiments of the present invention have been described above. The present invention is not limited to these embodiments, as a matter of course, and various changes and modifications can be made within the spirit and scope of the present invention. More specifically, the present invention may be applied to a system constituted by a plurality of devices, or to an apparatus constituted by a single device.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-119711, filed Jun. 12, 2015, which is hereby incorporated by reference herein in its entirety.

What is claimed is:

1. An image processing apparatus comprising:
a processor; and
a memory storing a program including instructions executed by the processor,
wherein the processor and the memory are operatively coupled to function as:
a dark correction unit configured to obtain a dark corrected image by removing a dark image obtained in a state without radiation irradiation from an object image obtained by radiation irradiation;
an addition value obtaining unit configured to analyze pixel values included in a plurality of dark corrected images and, based on an analysis result of the pixel values including a negative pixel value, obtain an addition value used to correct the negative pixel value; and
an adding unit configured to add the addition value to the pixel values of the dark corrected image.

2. The apparatus according to claim 1, wherein the processor and the memory are operatively coupled to function as an evaluation value obtaining unit configured to analyze the pixel values included in the plurality of dark corrected images and obtain the analysis result of the pixel values including the negative pixel value as an evaluation value,
wherein the addition value obtaining unit obtains the addition value used to correct the negative pixel value based on a variation in the evaluation value caused by an elapse of time.

3. The apparatus according to claim 2, wherein the addition value obtaining unit obtains, as the variation in the evaluation value caused by the elapse of time, a difference between an evaluation value of a current frame as a processing target and an addition value of a preceding frame to the current frame, and obtains the addition value of the current frame based on a result of determining whether an absolute value of the difference exceeds a threshold.

4. The apparatus according to claim 3, wherein if the absolute value of the difference between the evaluation value of the current frame and the addition value of the preceding frame to the current frame is not less than the threshold, and the difference between the evaluation value of the current frame and the addition value of the preceding frame is a negative value smaller than 0, the addition value obtaining unit corrects the evaluation value of the current frame based on a value obtained by subtracting the threshold from the addition value of the preceding frame.

5. The apparatus according to claim 3, wherein if the absolute value of the difference between the evaluation value of the current frame and the addition value of the preceding frame to the current frame is not less than the threshold, and the difference between the evaluation value of the current frame and the addition value of the preceding frame is not less than 0, the addition value obtaining unit corrects the evaluation value of the current frame based on a value obtained by adding the threshold to the addition value of the preceding frame.

6. The apparatus according to claim 4, wherein if the absolute value of the difference does not exceed the threshold, the addition value obtaining unit obtains the addition value of the current frame based on the addition value of the preceding frame and the evaluation value of the current frame, and
if the absolute value of the difference is not less than the threshold, the addition value obtaining unit obtains the addition value of the current frame based on the addition value of the preceding frame and the corrected evaluation value.

7. The apparatus according to claim 2, wherein the evaluation value obtaining unit analyzes the pixel values included in the dark corrected image, and obtains an analysis result of a predetermined ratio of pixel values including a negative pixel value as the evaluation value, and
the addition value obtaining unit obtains the addition value used to correct the negative pixel value based on a result of determining whether the variation in the evaluation value caused by the elapse of time exceeds a threshold.

8. An image processing apparatus comprising:
a processor, and
a memory storing a program including instructions executed by the processor,
wherein the processor and the memory being operatively coupled to function as:
a dark correction unit configured to obtain a dark corrected image by removing a dark image obtained in a state without radiation irradiation from an object image obtained by radiation irradiation;
an evaluation value obtaining unit configured to analyze pixel values included in the dark corrected image and obtain an analysis result of the pixel values including a negative pixel value as an evaluation value;
a statistic information obtaining unit configured to obtain statistic information based on a plurality of evaluation values obtained along with an elapse of time;
an addition value obtaining unit configured to obtain an addition value used to correct the negative pixel value based on a variation in the evaluation values with respect to the statistic information; and
an adding unit configured to add the addition value to the pixel values of the dark corrected image.

9. The apparatus according to claim 8, wherein the evaluation value obtaining unit
generates a histogram of pixel values for the dark corrected image if the pixel values of the dark corrected image include a negative pixel value smaller than 0,
obtains pixel values of points corresponding to a predetermined ratio from a lower side of the histogram, and
obtains the evaluation value based on a result of determining whether the obtained pixel value is a negative value smaller than 0.

10. The apparatus according to claim 9, wherein the evaluation value obtaining unit generates the histogram after excluding, from all pixels of a detection unit configured to detect radiation, pixel values in a region where the radiation is blocked.

11. The apparatus according to claim 9, wherein the evaluation value obtaining unit multiplies a total number of pixels of a detection unit configured to detect the radiation by the predetermined ratio, and specifies the pixel values of the points corresponding to the predetermined ratio.

12. The apparatus according to claim 9, wherein if the obtained pixel value is smaller than 0 based on a determination result, the evaluation value obtaining unit obtains an absolute value of the pixel value as the evaluation value.

13. The apparatus according to claim 9, wherein if the obtained pixel value is not less than 0 based on the determination result, the evaluation value obtaining unit obtains the evaluation value set to 0.

14. The apparatus according to claim 9, wherein if the negative pixel value is not included in the dark corrected image, the evaluation value obtaining unit obtains the evaluation value set to 0.

15. The apparatus according to claim 8, wherein the evaluation value obtaining unit analyzes the pixel values included in the dark corrected image, and obtains the analysis result of a predetermined ratio of the pixel values including the negative pixel value as the evaluation value, and
wherein the addition value obtaining unit obtains the addition value used to correct the negative pixel value based on a result of determining whether the variation in the evaluation values with respect to the statistic information exceeds a threshold.

16. The apparatus according to claim 15, wherein if the variation in the evaluation values with respect to the statistic information does not exceed the threshold based on the determination result, the addition value obtaining unit obtains, as the addition value, the evaluation value obtained by the evaluation value obtaining unit.

17. The apparatus according to claim 15, wherein if the variation in the evaluation values with respect to the statistic information is not less than the threshold based on the determination result, the addition value obtaining unit obtains, as the addition value, the statistic information obtained by the statistic information obtaining unit.

18. The apparatus according to claim 15, wherein the statistic information obtaining unit obtains, as the statistic information, an average value based on evaluation values of a plurality of frames captured in the past and a standard deviation based on the evaluation values, and obtains the threshold based on the standard deviation, and wherein the addition value obtaining unit obtains the addition value used to correct the negative pixel value based on a result of determining whether an absolute value of a difference between the average value and an evaluation value of a current frame as a processing target exceeds the threshold.

19. A radiation imaging apparatus comprising:
a processor; and
a memory storing a program including instructions executed by the processor,
wherein the processor and the memory being operatively coupled to function as:
 a radiation generator configured to generate radiation;
 a detection unit configured to detect the radiation; and
 an image processing apparatus configured to process image data detected by the detection unit,
 the image processing apparatus comprising:
  a dark correction unit configured to obtain a dark corrected image by removing a dark image obtained in a state without radiation irradiation from an object image obtained by radiation irradiation;
  an addition value obtaining unit configured to analyze pixel values included in a plurality of dark corrected images and, based on an analysis result of the pixel values including a negative pixel value, obtain an addition value used to correct the negative pixel value; and
  an adding unit configured to add the addition value to the pixel values of the dark corrected image.

20. An image processing method comprising:
obtaining a dark corrected image by removing a dark image obtained in a state without radiation irradiation from an object image obtained by radiation irradiation;
analyzing pixel values included in a plurality of dark corrected images and, based on an analysis result of the pixel values including a negative pixel value, obtaining an addition value used to correct the negative pixel value; and
adding the addition value to the pixel values of the dark corrected image.

21. An image processing method comprising:
obtaining a dark corrected image by removing a dark image obtained in a state without radiation irradiation from an object image obtained by radiation irradiation;
analyzing pixel values included in the dark corrected image and obtaining an analysis result of the pixel values including a negative pixel value as an evaluation value;
obtaining statistic information based on a plurality of evaluation values obtained along with an elapse of time;
obtaining an addition value used to correct the negative pixel value based on a variation in the evaluation values with respect to the statistic information; and
adding the addition value to the pixel values of the dark corrected image.

22. A non-transitory computer-readable storage medium storing a program that causes a computer to function as each unit of an image processing apparatus, the image processing apparatus comprising:
a dark correction unit configured to obtain a dark corrected image by removing a dark image obtained in a state without radiation irradiation from an object image obtained by radiation irradiation;
an addition value obtaining unit configured to analyze pixel values included in a plurality of dark corrected images and, based on an analysis result of the pixel values including a negative pixel value, obtain an addition value used to correct the negative pixel value; and
an adding unit configured to add the addition value to the pixel values of the dark corrected image.

* * * * *